(12) United States Patent
Smith et al.

(10) Patent No.: US 10,271,870 B2
(45) Date of Patent: Apr. 30, 2019

(54) COAXIAL CONTRA-ROTATING CUTTING ASSEMBLY

(71) Applicant: Volcano Corporation, San Diego, CA (US)

(72) Inventors: Torrey P Smith, San Diego, CA (US); Douglas E Rowe, San Diego, CA (US); Paul Quentin Escudero, San Diego, CA (US); August Christopher Pombo, San Diego, CA (US)

(73) Assignee: VOLCANO CORPORATION, San Diego, CA (US)

( * ) Notice: Subject to any disclaimer, the term of this patent is extended or adjusted under 35 U.S.C. 154(b) by 320 days.

(21) Appl. No.: 15/198,899

(22) Filed: Jun. 30, 2016

(65) Prior Publication Data

US 2017/0000518 A1    Jan. 5, 2017

Related U.S. Application Data

(60) Provisional application No. 62/186,633, filed on Jun. 30, 2015.

(51) Int. Cl.
*A61B 17/3207* (2006.01)
*A61B 17/00* (2006.01)
*A61B 17/22* (2006.01)

(52) U.S. Cl.
CPC ........... *A61B 17/320758* (2013.01); *A61B 2017/00292* (2013.01); *A61B 2017/00685* (2013.01);
(Continued)

(58) Field of Classification Search
CPC ...... A61B 17/320016; A61B 17/32002; A61B 17/320758; A61B 17/32053; A61B 17/3207; A61B 17/320725; A61B 17/32075; A61B 17/1637; A61B 17/16; A61B 17/1604; A61B 17/1615; A61B 17/162; A61B 17/1622; A61B 17/1624; A61B 17/1631; A61B 2017/320024; A61B 2017/320028; A61B 2017/320032; A61B 2017/320775; A61B 2017/320741; A61B 2017/320766; A61B 2017/1602; A61B 1/00066; A61B 1/00068; A61B 1/00121; A61B 1/00124; A61B 1/00126; A61B 1/00128; A61B 1/00131; A61B 1/012;
(Continued)

(56) References Cited

U.S. PATENT DOCUMENTS

| 4,306,570 A | * | 12/1981 | Matthews | ............ A61B 10/025 408/206 |
| 2008/0045986 A1 | * | 2/2008 | To | ............ A61B 17/320708 606/159 |

* cited by examiner

*Primary Examiner* — Eric Rosen
*Assistant Examiner* — Chima Igboko

(57) ABSTRACT

The invention generally relates to intraluminal procedures, and, more particularly, to a contra-rotating cutting assembly for use with an atherectomy device to remove occlusive material from an occluded lumen, such as a blood vessel or other body lumen. The contra-rotating cutting assembly includes a rotatable housing having a distal end, an opposing proximal end and a lumen extending between the distal and proximal ends. The housing is configured to rotate about a longitudinal axis in a first direction. The cutting assembly further includes a rotatable cutter head positioned within at least a portion of the lumen of the housing and in coaxial alignment with the housing. The cutter head is configured to rotate about the longitudinal axis in a second direction opposite the first direction.

9 Claims, 4 Drawing Sheets

(52) U.S. Cl.
CPC .............. *A61B 2017/00778* (2013.01); *A61B 2017/22094* (2013.01); *A61B 2017/320716* (2013.01); *A61B 2017/320775* (2013.01)

(58) Field of Classification Search
CPC ....... A61B 1/0125; A61B 1/018; A61B 1/005; A61B 1/0052; B23Q 5/04; B23Q 5/041; B23Q 5/043; B23Q 5/046; B23Q 5/048; B23Q 5/12; B23Q 5/162; A61M 2025/0175; A61M 2025/0177; A61M 2025/0183; A61M 2025/0188; A61M 2025/0197; A61M 2025/09116; A61M 2025/09125; A61M 25/01; A61M 25/0194; A61M 25/09; B23P 15/14; B21D 53/28; Y10T 29/49464; Y10T 29/49465; A61C 1/18; A61C 1/185; A61C 1/02; A61C 1/05; A61C 1/06
USPC .......................................................... 30/276
See application file for complete search history.

COAXIAL CONTRA-ROTATING CUTTING ASSEMBLY

CROSS REFERENCE TO RELATED APPLICATIONS

This application claims the benefit of and priority to U.S. Provisional Patent Application Ser. No. 62/186,633, filed Jun. 30, 2015, the contents of which are incorporated by reference herein in their entirety.

FIELD OF THE INVENTION

The present invention generally relates to intraluminal procedures, and, more particularly, to a contra-rotating cutting assembly for use with an atherectomy device to remove occlusive material from an occluded lumen, such as a blood vessel or other body lumen.

BACKGROUND

Millions of people suffer and die from various forms of cardiovascular disease, including coronary artery disease and peripheral vascular disease (also known as peripheral arterial disease). Coronary artery disease and peripheral vascular disease can arise due to the narrowing of the arteries by atherosclerosis (also called arteriosclerosis). Atherosclerosis is a progressive disease and occurs when fat, cholesterol, and other substances build up on the walls of arteries and form fleshy or hard/calcified structures called plaques/lesions. As plaque forms within the native arterial wall, the artery may narrow and become less flexible, which may make it more difficult for blood to flow therethrough. In the peripheral arteries, the plaque is typically not localized, but can extend in length along the axis of the artery for as much as 10 mm or more (in some instance up to 400 mm or more).

Coronary artery disease develops when the coronary arteries become damaged or diseased, generally as a result of plaque deposits within the arteries. Such plaque deposits result in narrowing of the arteries, decrease in blood flow to the heart, and eventually cause chest pain (angina), shortness of breath, or other coronary artery disease signs and symptoms. A complete blockage can cause a heart attack and death. Peripheral vascular disease develops when narrowed arteries reduce blood flow to parts of the body outside of the hearth and brain, such as the limbs. Upon developing peripheral vasculature disease, a person's extremities, usually their legs, fail to receive enough blood flow to keep up with demand. Complications of peripheral vasculature disease may include activity-induced claudication sores that do not heal, ulcers, gangrene, tissue loss, or infections in the extremities. In rare cases, if left untreated, amputation may be necessary.

Endovascular clearing procedures to reduce or remove the obstructions from within an artery are known. Vascular specialists can now choose from a variety of endovascular technologies, ranging from traditional approaches, such as percutaneous transluminal balloon angioplasty (PTA) and self-expanding nitinol stents to newer advancements, including atherectomy catheters and drug-eluting balloons and stents. In balloon angioplasty, for example, a physician may advance a collapsed, intravascular balloon catheter into a narrowed artery, and may inflate the balloon to macerate and/or displace plaque against the vessel wall. A successful angioplasty may help reopen the artery and allow for improved blood flow. Often, balloon angioplasty is performed in conjunction with the placement of a stent or scaffold structure within the artery to help minimize re-narrowing of the artery. Balloon angioplasty, however, can stretch the artery and induce scar tissue formation, while the placement of a stent can cut arterial tissue and also induce scar tissue formation. Scar tissue formation may lead to restenosis of the artery. In some instances, balloon angioplasty can also rip the vessel wall.

Atherectomy is another treatment methodology for atherosclerosis. Atherectomy involves the use of an intravascular device to mechanically remove (e.g., debulk) plaque from the wall of the artery, thereby reducing the risk of stretching, cutting, or dissecting the arterial wall and causing tissue damage that leads to restenosis. In some instances, atherectomy may be used to treat restenosis by removing scar tissue.

Current atherectomy treatments suffer from structural and performance limitations. For example, some current atherectomy devices with rotating burrs generally are not configured to capture particles that are released as the burr grinds/sands tissue, which may result in diminished downstream blood flow resulting from particle residue. Additionally, these rotating burrs may cause hemolysis, and are generally limited as an adjunct therapy to angioplasty. Other systems may include expandable cutters with foldable/movable cutting wings and vacuum-driven aspiration supplied via a vacuum pump, which may cause the artery to collapse on to the cutter and perforate the arterial wall. Other atherectomy systems may include a side-window eccentric cutter and distal nosecone which receives material from the cutter. Because the nosecone can only hold a limited volume of plaque, a surgeon may need to repeatedly withdraw the cutter and flush plaque and other material from the nosecone.

SUMMARY

The invention is directed to a cutting assembly configured to maximize the removal and clearing of obstructions or occlusive material within body lumens, particularly the vasculature. The features of the cutting assembly of the present invention allow for improved control over the removal of occlusive materials and further ensure collection of a more cohesive unit of material, thereby overcoming drawbacks of current atherectomy devices, which lack the ability to effectively capture additional particles of material that may otherwise dislodge during a procedure and may lead to embolization of a downstream vessel.

The cutting assembly of the present disclosure is able to overcome the drawbacks of current atherectomy devices by providing a rotatable cutter head and a separately rotatable housing, each of which is capable of rotating in opposite directions relative to one another along a common axis so as to allow contra-rotation. The contra-rotatable cutting assembly of the present disclosure provides a distinct means of cutting and conveying occlusive material and addresses the drawbacks of current devices. In particular, rotation of the housing in an opposing direction of the cutter head may reduce or entirely prevent some effects of the rotating cutter head. For example, rotation of the housing may cancel out cutter-induced swirl within the bloodstream. Additionally, contra-rotation may further increase the amount of material captured. For example, rotation of the housing in an opposing direction may reduce the radial velocity component of excised tissue particles (e.g., flinging of particles caused by cutter head during cutting), thereby lessening the risk of particle loss and further improves embolic capture performance. In some embodiments, the housing may include a cutting edge at a distal end, such that the housing may further function as a coring cutter upon contact between the distal end and occlusive material, thereby improving the cutting effectiveness of the cutting assembly and may further increase the ability of an atherectomy device to clear long total occlusions in a single pass with little or no clogging.

In one aspect, the present invention provides a contra-rotatable cutting assembly for cutting occlusive material from within a body lumen. The cutting assembly includes a rotatable housing having a distal end, an opposing proximal end and a lumen extending between the distal and proximal ends. The housing is configured to rotate about a longitudinal axis in a first direction. The cutting assembly further includes a rotatable cutter head positioned within at least a portion of the lumen of the housing and in coaxial alignment with the housing. The cutter head is configured to rotate about the longitudinal axis in a second direction opposite the first direction.

The cutting assembly further includes a contra-rotation gear assembly positioned within the housing and configured to drive rotation of at least the housing in response to rotation of the cutter head. In some embodiments, the gear assembly includes a first crown gear coupled to the cutter head and configured to rotate about the longitudinal axis in the second direction, at least one spur gear in engagement with the first crown gear and configured to rotate in response to rotation of the first crown gear, and a second crown gear in engagement with the at least one spur gear and coupled to the housing. The second crown gear is configured to rotate about the longitudinal axis in the first direction in response to rotation of the at least one spur gear to thereby impart rotational force upon the housing and cause the housing to rotate about the longitudinal axis in the first direction opposite the second direction of rotation of the cutter head.

The cutter head generally includes a cutting edge or surface configured to excise, or otherwise shear, occlusive material upon contact therewith. For example, in some embodiments, cutter head includes at least one helical flute having a cutting edge configured to excise or shear occlusive material upon contact therewith. The at least one helical flute may be configured to convey excised material along a length of the cutter head in a direction toward the proximal end of the housing in response to rotation of the cutter head. In some embodiments, the distal end of the housing may include a cutting surface or edge configured to excise or shear occlusive material upon contact therewith. Accordingly, the housing may effectively function as a coring device.

The cutting assembly may be used to clear or otherwise clear obstructions or occlusive material within a variety of body lumens, particularly vasculature. Accordingly, the cutting assembly may be appropriately sized so as to fit with different sized body lumens (e.g., small, medium, large arteries). In some embodiments, the housing has an outer diameter in the range of 1.5 mm to 8 mm. In some embodiments, the housing has an outer diameter in the range of 2 mm to 3 mm. Yet still, in some embodiments, the housing has an outer diameter of 2.4 mm.

The cutting assembly further includes a ferrule coupled to the proximal end of the housing and configured to couple the cutting assembly to an atherectomy device. Furthermore, the cutter head is configured to be coupled to a rotating member of an atherectomy device configured to transmit rotational energy to the cutter head and cause the cutter head to rotate about the longitudinal axis.

In another aspect, the present invention provides a device for cutting and removing occlusive material from within a body lumen. The device includes a catheter body having a distal end, a proximal end and a lumen extending there between. The catheter body is sized and configured for axial advancement within a body lumen. The device further includes a torque shaft positioned within at least a portion of the lumen of the catheter and coupled to a rotating mechanism (e.g., an electric, pneumatic, fluid, gas, or other motor). The device further includes a contra-rotatable cutting assembly positioned at the distal end of the catheter body and coupled to the torque shaft to receive rotational energy therefrom. The cutting assembly includes a rotatable housing having a distal end, an opposing proximal end and a lumen extending between the distal and proximal ends. The housing is configured to rotate about a longitudinal axis in a first direction. The cutting assembly further includes a rotatable cutter head positioned within at least a portion of the lumen of the housing and in coaxial alignment with the housing. The cutter head is configured to rotate about the longitudinal axis in a second direction opposite the first direction. The cutting assembly further includes a contra-rotation gear assembly positioned within the housing and configured to drive rotation of at least the housing in response to rotation of the torque shaft and cutter head.

In some embodiments, the gear assembly may include a first crown gear, a second crown gear, and at least one spur gear positioned between and in engagement with both the first and second crown gears. The first crown gear is coupled to at least one of the torque shaft and cutter head and configured to rotate about the longitudinal axis in the second direction in response to rotation of the torque shaft. The at least one spur gear is configured to rotate in response to rotation of the first crown gear and thereby cause the second crown gear to rotate about the longitudinal axis in the first direction. The second crown gear is coupled to the housing and configured to impart rotational force thereto to cause the housing to rotate about the longitudinal axis in the first direction opposite the second direction of rotation of the cutter head.

As previously described, the cutter head generally includes a cutting edge or surface configured to excise, or otherwise shear, occlusive material upon contact therewith. For example, in some embodiments, cutter head includes at least one helical flute having a cutting edge configured to excise or shear occlusive material upon contact therewith. The at least one helical flute may be configured to convey excised material along a length of the cutter head in a direction toward the proximal end of the housing in response to rotation of the cutter head. The torque shaft may include an external threading helically wound about the torque shaft along a length thereof and configured to convey material conveyed into the housing by the cutter head further proximally along the catheter body for discharge. Accordingly, the torque shaft may further serve as an auger type system or an Archimedes-type screw that conveys the debris and material generated during the procedure away from the operative site.

DETAILED DESCRIPTION

Figure 1:
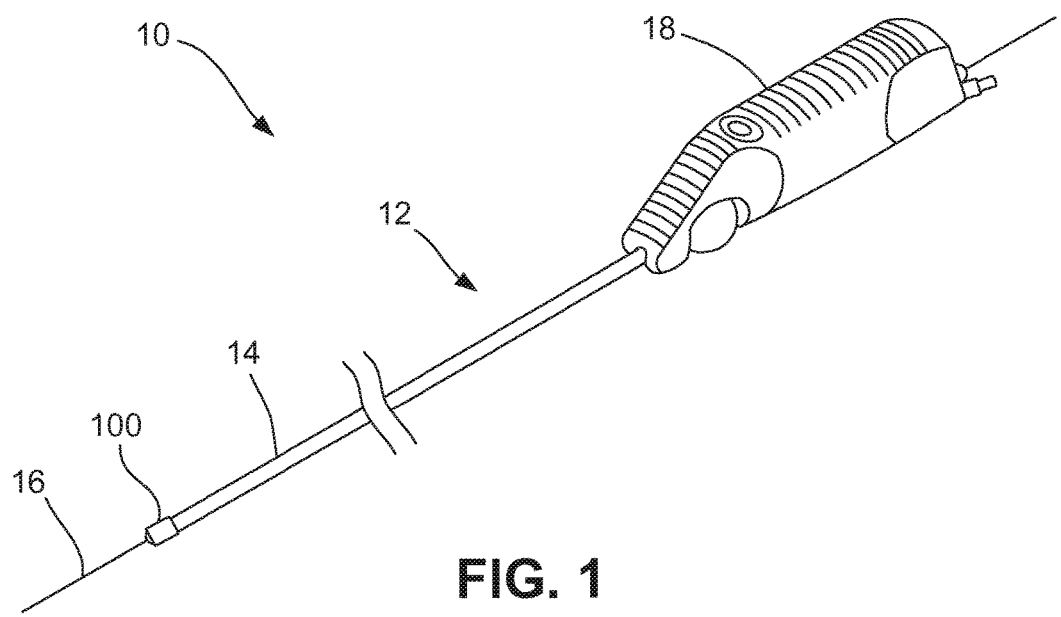
FIG. 1 is a perspective view of an atherectomy system including a contra-rotatable cutting assembly consistent with the present disclosure.

The present invention is directed to a cutting assembly configured to maximize the removal and clearing of obstructions or occlusive material within body lumens, particularly the vasculature. The features of the cutting assembly of the present invention allow for improved control over the removal of occlusive materials and further ensure collection of a more cohesive unit of material, thereby overcoming drawbacks of current atherectomy devices, which lack the ability to effectively capture additional particles of material that may otherwise dislodge during a procedure and may lead to embolization of a downstream vessel.

By way of overview, the present invention provides a contra-rotatable cutting assembly for cutting occlusive material from within a body lumen. The cutting assembly includes a rotatable housing having a distal end, an opposing proximal end and a lumen extending between the distal and proximal ends. The housing is configured to rotate about a longitudinal axis in a first direction. The cutting assembly further includes a rotatable cutter head positioned within at least a portion of the lumen of the housing and in coaxial alignment with the housing. The cutter head is configured to rotate about the longitudinal axis in a second direction opposite the first direction. The cutting assembly further includes a contra-rotation gear assembly positioned within the housing and configured to drive rotation of at least the housing in response to rotation of the cutter head. In some embodiments, the gear assembly includes a first crown gear coupled to the cutter head and configured to rotate about the longitudinal axis in the second direction, at least one spur gear in engagement with the first crown gear and configured to rotate in response to rotation of the first crown gear, and a second crown gear in engagement with the at least one spur gear and coupled to the housing. The second crown gear is configured to rotate about the longitudinal axis in the first direction in response to rotation of the at least one spur gear to thereby impart rotational force upon the housing and cause the housing to rotate about the longitudinal axis in the first direction opposite the second direction of rotation of the cutter head.

The cutter head generally includes a cutting edge or surface configured to excise, or otherwise shear, occlusive material upon contact therewith. For example, in some embodiments, cutter head includes at least one helical flute having a cutting edge configured to excise or shear occlusive material upon contact therewith. The at least one helical flute may be configured to convey excised material along a length of the cutter head in a direction toward the proximal end of the housing in response to rotation of the cutter head. In some embodiments, the distal end of the housing may include a cutting surface or edge configured to excise or shear occlusive material upon contact therewith. Accordingly, the housing may effectively function as a coring device.

The cutting assembly may be used to clear or otherwise clear obstructions or occlusive material within a variety of body lumens, particularly vasculature. Accordingly, the cutting assembly may be appropriately sized so as to fit with different sized body lumens (e.g., small, medium, large arteries). In some embodiments, the housing has an outer diameter in the range of 1.5 mm to 8 mm. In some embodiments, the housing has an outer diameter in the range of 2 mm to 3 mm. Yet still, in some embodiments, the housing has an outer diameter of 2.4 mm.

Accordingly, the cutting assembly of the present disclosure is able to overcome the drawbacks of current atherectomy devices by providing a rotatable cutter head and a separately rotatable housing, each of which is capable of rotating in opposite directions relative to one another along a common axis so as to allow contra-rotation. The contra-rotatable cutting assembly of the present disclosure provides a distinct means of cutting and conveying occlusive material and addresses the drawbacks of current devices. In particular, rotation of the housing in an opposing direction of the cutter head may reduce or entirely prevent some effects of the rotating cutter head. For example, rotation of the housing may cancel out cutter-induced swirl within the bloodstream. Additionally, contra-rotation may further increase the amount of material captured. For example, rotation of the housing in an opposing direction may reduce the radial velocity component of excised tissue particles (e.g., flinging of particles caused by cutter head during cutting), thereby lessening the risk of particle loss and further improves embolic capture performance. In some embodiments, the housing may include a cutting edge at a distal end, such that the housing may further function as a coring cutter upon contact between the distal end and occlusive material, thereby improving the cutting effectiveness of the cutting assembly and may further increase the ability of an atherectomy device to clear long total occlusions in a single pass with little or no clogging.

FIG. 1 is a perspective view of an atherectomy system 10 including a contra-rotatable cutting assembly 100 consistent with the present disclosure. Described herein are various embodiments of a cutting assembly for use in removing occlusive material, such as for performing an atherectomy. Specifically, the various elements described here may be configured to be incorporated into any of the atherectomy devices described in any one of U.S. patent application Ser. Nos. 11/551,191; 11/551,193; 11/551,203; 11/567,715; 13/652,352; 13/691,485; 14/069,303; and Ser. No. 14/329,805, the content of each of which is hereby incorporated by reference its entirety. Accordingly, the atherectomy device 12, to which a cutting assembly described herein may be coupled, may generally include a handle and at least one catheter connecting the handle and the cutter assembly. The atherectomy device may include a torque shaft, which may extend through the catheter, and which may be configured to rotate a cutter relative to the catheter. In some instances, the torque shaft may include a conveyor member configured to move cut occlusive material along the torque shaft, as will be described in greater detail herein.

As shown in FIG. 1, the atherectomy device 12 may include an elongated catheter body 14 sized and configured to be advanced over a guide wire 16 within a blood vessel or other body lumen from an external percutaneous access site. While shown in FIG. 1 (and FIG. 7) as being advanced over a guide wire 16, it should be appreciated that in some variations, the atherectomy device 12 may be advanced without a guide wire, and in other variations the atherectomy device 12 may comprise a guide wire attached to a distal portion of the atherectomy device 12. The atherectomy device 12 may also include a handle 18, which may be coupled to the proximal (i.e., closest to the user) end of the catheter 14. The handle 18 may be sized and configured to be held and manipulated by a user outside the patient's body. The atherectomy device 12 may further comprise a cutter assembly 100 at the distal end of the catheter 14. Generally, the cutter assembly 100 may act to cut and capture occlusive material, and thereby remove the occlusive material from the vessel, which may open the vessel to blood flow.

Figure 2:
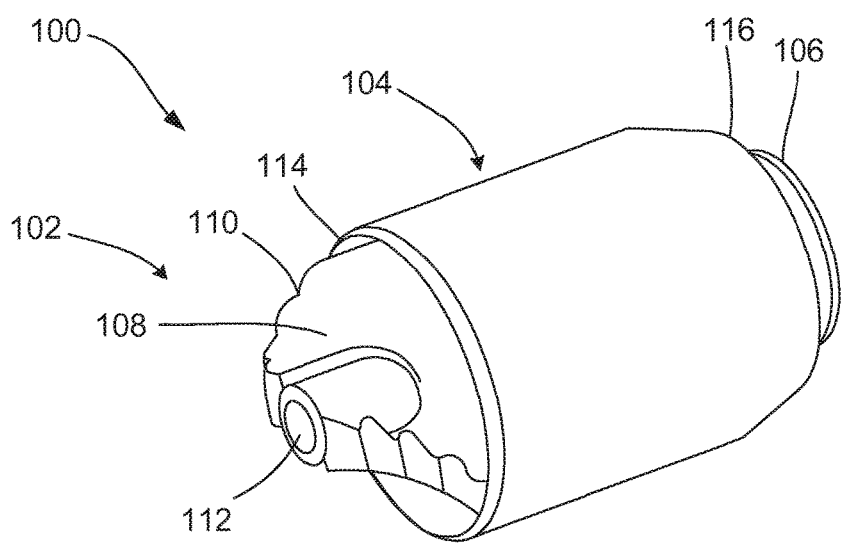
FIG. 2 is an enlarged perspective view of a contra-rotatable cutting assembly consistent with the present disclosure.

FIG. 2 is an enlarged perspective view of a contra-rotatable cutting assembly 100 consistent with the present disclosure. As shown, the cutting assembly 100 includes a rotatable cutter head 102 which may be at least partially housed within a rotatable housing 104. The cutting assembly 100 further includes a ferrule 106 configured to join one or more portions of the cutting assembly 100 (e.g., the housing 104) to a distal end of the catheter 14. As shown, the cutter head 102 includes at least two helical flutes 108, each of which includes a cutting edge 110 configured to excise, or otherwise shear, material upon contact therewith. The helical flutes 108 may be shaped and/or sized so as to convey excised material along a length of the cutter head 102 and in a direction toward the housing 104 as the cutter head 102 rotates. The cutter head 102 further includes a lumen or throughhole 112 configured to receive the guide wire 16.

It should be noted that the cutter head 102 may include any number of flutes 108 and/or cutting edges 110 in any contemplated configuration and/or design. For example, while the cutting edges 110 of the helical cutting flutes 108 are shown as curving in a clockwise helical direction when viewed from the distal end (see FIG. 6), it should be appreciated that in other variations the cutting edges 110 of the cutting flutes 108 may have a counterclockwise helical curve when viewed from the distal end. Similarly, while the cutter head 102 is shown has having two cutting flutes 108, it should be appreciated that in other variations, the cutter head 102 may comprise any suitable number of cutting flutes (e.g., one, two, three, four, or more cutting flutes).

Furthermore, the geometry of the cutting flutes 108 may be characterized with reference to a combination of angles (or ranges of angles), including rake angle, relief angle, and flute angle. The rake angle may describe the angle of the cutting edge 310 relative to the material to be cut, while the relief angle may be defined as the angle measured between (i) the tangent drawn from the most radially distant edge of the cutting edge 110 and (ii) the tangent drawn along the outer face of the cutting flute 108. Generally, a smaller relief angle may form a more tangential interface with a tissue surface during cutting, which may reduce the likelihood that a cutting edge may snag or otherwise catch on tissue during cutting. A larger relief angle may provide more aggressive cutting.

The housing 104 generally includes a distal end 114, a proximal end 116 (coupled to the ferrule 106) and a lumen extending there between. The housing 104 may be open at its distal-most end 114 such that the distal-most end of the cutter head 102 may project a distance distally from the housing 104. Accordingly, at least a portion of the cutter head 102 is enclosed within the housing 104. More specifically, the cutter head 102 is positioned within the lumen of the housing and in coaxial alignment therewith, such that the cutter head 102 and housing 104 share a common axis (longitudinal axis A). As will be described in greater detail herein, the cutter head 102 and housing 104 are configured to rotate about the longitudinal axis X in opposing directions, thereby providing contra-rotation which provides an improved means of cutting and removing material during a procedure.

Figure 3:
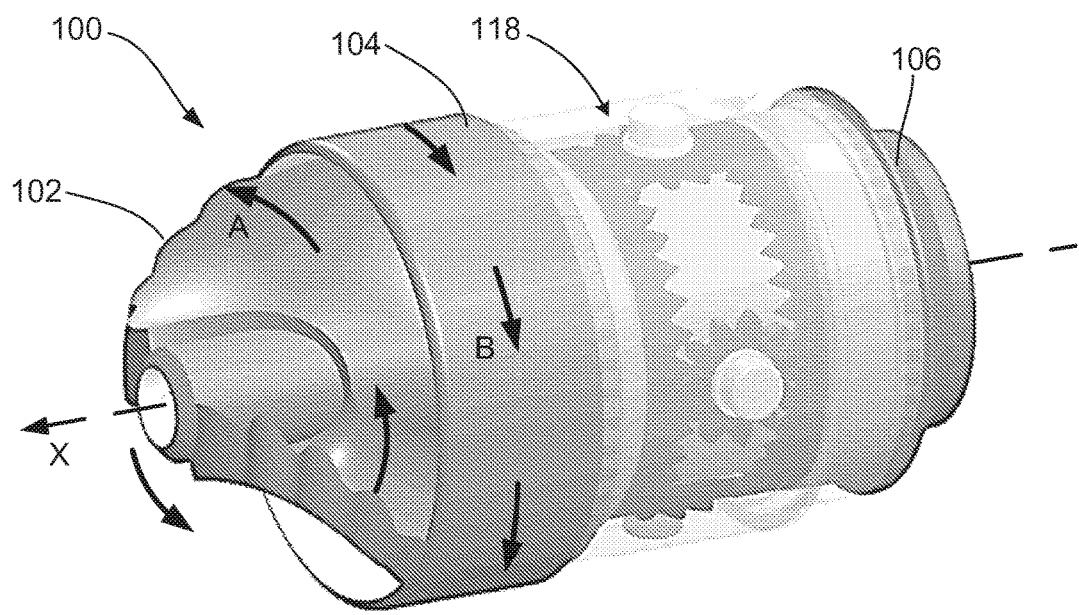
FIG. 3 is an enlarged perspective view of the cutting assembly of FIG. 2, a portion of which is shown in phantom illustrating the contra-rotation gear assembly consistent with the present disclosure.
Figure 4:
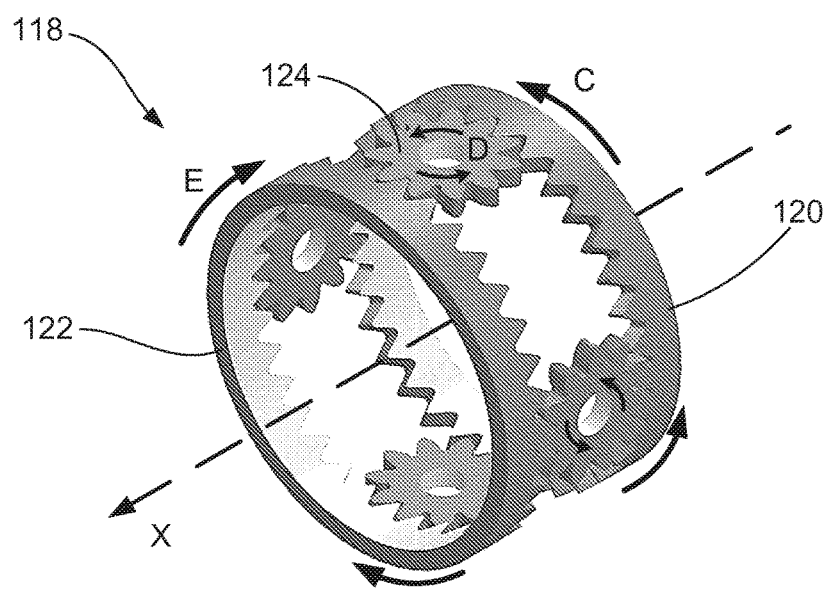
FIG. 4 is an enlarged perspective view of the contra-rotation gear assembly of FIG. 3.

FIG. 3 is an enlarged perspective view of the cutting assembly 100. A portion of the housing 104 is shown in phantom so as to illustrate a contra-rotation gear assembly 118 positioned within the housing 104 and configured to provide contra-rotation of the cutter head 102 and housing 104 relative to one another. FIG. 4 is an enlarged perspective view of the contra-rotation gear assembly 18. As shown in FIG. 3, during operation, the cutter head 102 and housing 104 are each configured to rotate about longitudinal axis X in opposite directions. For example, when viewed from the distal end (see FIG. 6) the cutter head 102 may be configured to rotate in a counter-clockwise direction, as indicated by arrow A, while the housing 104 may be configured to rotate in a clockwise direction, as indicated by arrow B, thereby resulting in contra-rotation, as both the cutter head 102 and housing 104 share a common axis X.

Referring to FIG. 4, the gear assembly 118 may generally include a first crown gear 120, a second crown gear 122, and one or more spur gears 124 positioned there between. As generally understood, the first and second crown gears 120, 122 are gears which have teeth that project at right angles to the face of the wheel or circular body of the gear. Accordingly, the first and second crown gears 120, 122 are a type of bevel gear where the pitch cone angle is 90 degrees. It should be noted that the first and second crown gears 120, 122 are coaxially aligned with the cutter head 102 and housing 104 (e.g., share common axis X), while each spur gear 124 is generally positioned along a perimeter and between the first and second crown gears 120, 122 and in engagement with the teeth of the first and second crown gears. The first crown gear 120 is generally coupled to the cutter head 102 (or the torque shaft driving the cutter head 102). Accordingly, rotation of the first crown gear 120 corresponds to rotation of the cutter head 102. Thus, upon movement of the cutter head 102, the first crown gear 120 is configured to rotate in the same direction, as indicated by arrow C. Each spur gear 124 in engagement with the first crown gear 120 is configured to rotate in response to rotation of the first crown gear 120. The spur gears 124 are configured to rotate about an axis that is generally perpendicular to the common axis X along which the first and second crown gears 120, 122 lie, as indicated by arrow D. The second crown gear 122 is also in engagement with the spur gears 124. Accordingly, the second crown gear 122 is configured to rotate about axis X in response to rotation of the spur gears 124 in a direction opposite the direction of the first crown gear 120, as indicated by arrow E. Thus, if the first crown gear 120 rotates in a clockwise direction, the spur gears 124 will force the second crown gear 122 to rotate in a counter-clockwise direction, and vice-a-versa. The second crown gear 122 is coupled to the housing 104 and configured to impart rotational force thereupon so as to cause the housing 104 to rotate in a corresponding direction. Accordingly, the contra-rotation gear assembly 118 is configured to cause contra-rotation of the cutter head 102 and housing 104 relative to one another.

Figure 5:
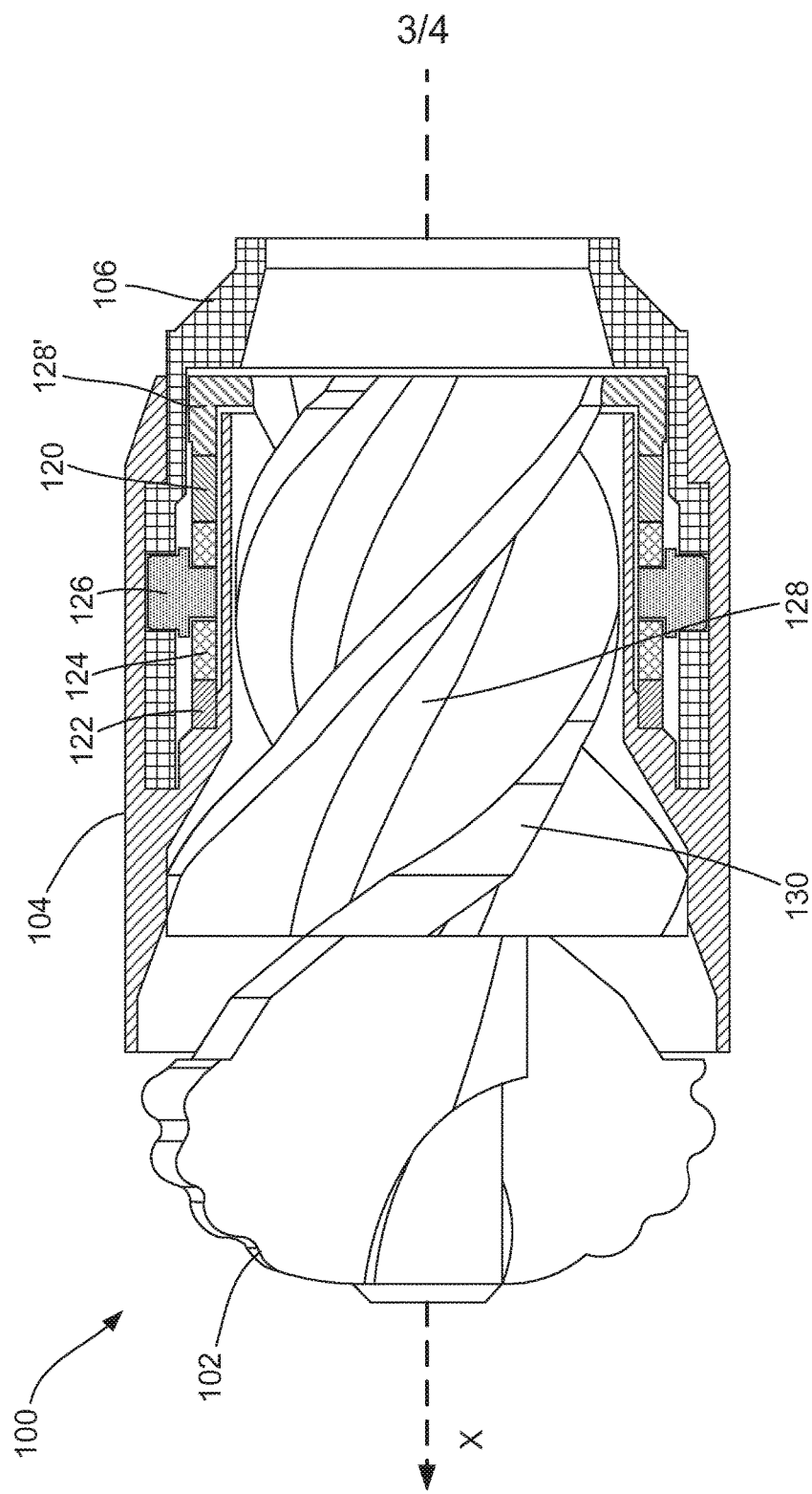
FIG. 5 is a side view, partly in section, of the cutting assembly of FIG. 2, illustrating the cutter head coupled to a torque shaft.

FIG. 5 is a side view, partly in section, of the cutting assembly 100 illustrating the cutter head 102 coupled to a rotating member of an atherectomy device configured to transmit rotational force to the cutter head 102. As previously described, the cutting assembly 100 may be a separate add-on type product and may be configured to be interchangeable with other cutting assemblies on a single atherectomy device, such as device 12 in FIG. 1. Accordingly, the cutting assembly 100 may be a "bolt-on" type upgrade and may be compatible with existing devices. For example, the cutting assembly 100 may simply be placed on a distal end of a catheter body 14 such that a rotating member, such as a torque shaft 128, may be received within the housing 104 and releasably coupled to the cutting head 102. Thus, the cutting head 102 may receive rotational force therefrom so as to cause the cutter head 102 and housing 104 to rotate relative to one another (via the contra-rotational gear assembly 118) for improved removal of an occlusive material. Thus, existing designs of atherectomy devices need not be changed, as the cutting assembly 100 of the present disclosure is compatible.

Figure 6:
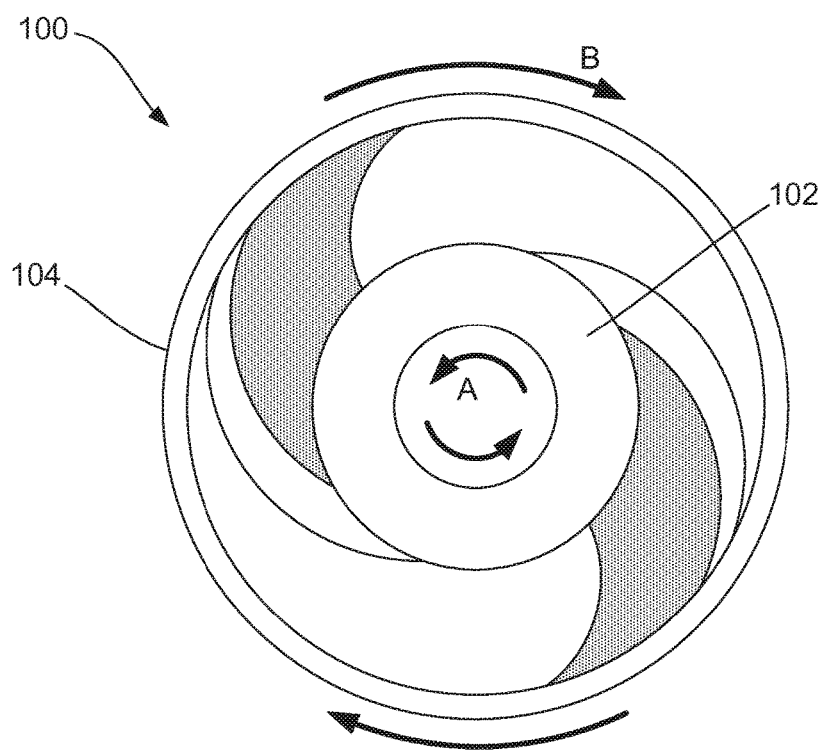
FIG. 6 is a front view (facing the distal end of the housing) of the cutting assembly of FIG. 2 illustrating contra-rotation of the cutting head and housing.

As shown in FIG. 5, a torque shaft 128, which may be positioned within the catheter 14, may rotationally connect a motor (not shown) to the cutter head 102. Specifically, the motor may rotate the torque shaft 128, which may in turn rotate the cutter 102 within the housing 104 about axis X. As previously described, the first crown gear 120 is coupled to at least one of the cutter head 102 and torque shaft 128. For example, the first crown gear 120 may be coupled to a portion 128' of the torque shaft 128, such that, upon rotation of the shaft 128, the first crown gear 120 rotates in a corresponding direction. The first crown gear 120 may be may be physically coupled to the cutter head 102 or torque shaft 128 by any known means (e.g., by adhesives, welding, or the like). As shown, the spur gears 124 are positioned between the first and second crown gears 120, 122 and may be generally held in a stationary position via a fastener 126, such as a pin or the like, while still allowing for rotation. Accordingly, upon rotation of the first crown gear 120, the spur gears 124 are configured to rotate, thereby causing the second crown gear 122 to rotate in an opposing direction relative to the first crown gear 120. The second crown gear 122 is physically coupled to a portion of the housing 104 so as to cause the housing 104 to correspondingly rotate in response to movement of the cutter head 102 and shaft 128. Accordingly, rotation of the shaft 128 causes both the cutter head 102 and housing 104 to rotate in a contra-rotational pattern for improved means of removing occlusive material from a body lumen, as shown in FIG. 6. It should be noted that the ferrule 106 may join the cutter assembly 100 and the catheter 14 so as to allow relative rotation between the catheter 100 and the housing 104. The housing 104 may be configured to rotate at the same speed as the cutter head 102. In some embodiments, the housing may be configured to rotate at a different speed than the cutter head.

As previously described, the torque shaft 128 may include a means of conveying debris and excised material from the cutter head 102 through the housing 104 and into the catheter 14. For example, as shown in FIG. 5, the torque shaft 128 may include an external threading 130 helically wound about the shaft along a length thereof, generally resembling an Archimedes screw. The external threading 140 may be useful in conveying cut occlusive material proximally along the catheter 14. Accordingly, when the cutter assembly 100 cuts and captures occlusive material (e.g., when the helical flutes 108 of the cutter head 102 convey captured occlusive materials to the external threading), the external threading may rotate in common with the torque shaft 128 so as to convey the cut and captures occlusive materials it receives from the cutter assembly 100 further back (proximally) along the catheter body 14 into the handle 18 for subsequent discharge.

Figure 7:
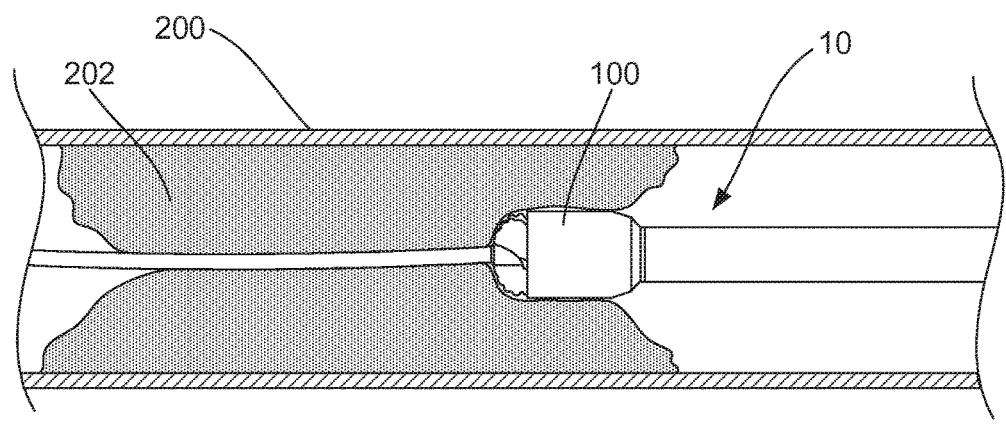
FIG. 7 depicts a side view, partly in section, of a body lumen and cutting and removal of occlusive material therefrom with an atherectomy system consistent with the present disclosure.

FIG. 7 depicts a side view, partly in section, of a body lumen 200 and cutting and removal of occlusive material 202 therefrom with an atherectomy system 10 consistent with the present disclosure. As shown, the cutting assembly 100 is configured to cut and remove occlusive material 202 from within a body lumen 200, such as an artery, so as to clear a passage to allow for improved blood flow. As generally understood, the cutting assembly 100 may be used to clear or otherwise clear obstructions or occlusive material within a variety of body lumens, particularly vasculature. Accordingly, the cutting assembly may be appropriately sized so as to fit with different sized body lumens (e.g., small, medium, large arteries). In some embodiments, the housing has an outer diameter in the range of 1.5 mm to 8 mm. In some embodiments, the housing has an outer diameter in the range of 2 mm to 3 mm. Yet still, in some embodiments, the housing has an outer diameter of 2.4 mm.

The cutting assembly of the present disclosure is able to overcome the drawbacks of current atherectomy devices by providing a rotatable cutter head and a separately rotatable housing, each of which is capable of rotating in opposite directions relative to one another along a common axis so as to allow contra-rotation. The contra-rotatable cutting assembly of the present disclosure provides a distinct means of cutting and conveying occlusive material and addresses the drawbacks of current devices. In particular, rotation of the housing in an opposing direction of the cutter head may reduce or entirely prevent some effects of the rotating cutter head. For example, rotation of the housing may cancel out cutter-induced swirl within the bloodstream. Additionally, contra-rotation may further increase the amount of material captured. For example, rotation of the housing in an opposing direction may reduce the radial velocity component of excised tissue particles (e.g., flinging of particles caused by cutter head during cutting), thereby lessening the risk of particle loss and further improves embolic capture performance. In some embodiments, the housing may include a cutting edge at a distal end, such that the housing may further function as a coring cutter upon contact between the distal end and occlusive material, thereby improving the cutting effectiveness of the cutting assembly and may further increase the ability of an atherectomy device to clear long total occlusions in a single pass with little or no clogging.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used.

Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A device for cutting and removing occlusive material from within a body lumen, said device comprising:
    a catheter body having a distal end, a proximal end and a lumen extending there between, said catheter body sized and configured for axial advancement within a body lumen;
    a torque shaft positioned within at least a portion of the lumen of the catheter body and coupled to a rotating mechanism; and
    a contra-rotatable cutting assembly positioned at said distal end of said catheter body and coupled to said torque shaft to receive rotational energy therefrom, said cutting assembly comprising:
        a rotatable housing having a distal end, an opposing proximal end and a lumen extending between the distal and proximal ends, said housing configured to rotate about a longitudinal axis in a first direction;
        a rotatable cutter head positioned within at least a portion of the lumen of said housing and in coaxial alignment with said housing, said cutter head configured to rotate about said longitudinal axis in a second direction opposite the first direction; and
        a contra-rotation gear assembly positioned within said housing and configured to drive rotation of at least said housing in response to rotation of said torque shaft and cutter head.

2. The device of claim 1, wherein said gear assembly comprises:
    a first crown gear coupled to at least one of said torque shaft and cutter head, said first crown gear configured to rotate about said longitudinal axis in said second direction in response to rotation of said torque shaft;
    at least one spur gear in engagement with said first crown gear and configured to rotate in response to rotation of said first crown gear; and
    a second crown gear in engagement with said at least one spur gear and coupled to said housing, said second crown gear configured to rotate about said longitudinal axis in said first direction in response to rotation of said at least one spur gear to thereby impart rotational force upon said housing and cause said housing to rotate about said longitudinal axis in said first direction opposite said second direction of rotation of said cutter head.

3. The device of claim 1, wherein said cutter head comprises at least one helical flute having a cutting edge configured to excise or shear occlusive material upon contact therewith and said at least one helical flute is configured to convey excised material along a length of said cutter head in a direction toward said proximal end of said housing in response to rotation of said cutter head.

4. The device of claim 3, wherein said torque shaft comprises an external threading helically wound about the torque shaft along a length thereof and configured to convey material conveyed into said housing by the cutter head further proximally along the catheter body for discharge.

5. The device of claim 1, wherein said distal end of said housing has a cutting surface or edge configured to excise or shear occlusive material upon contact therewith.

6. The device of claim 1, wherein each of said cutter head and torque shaft further comprises a lumen configured to receive a guide wire therethrough.

7. The device of claim 1, wherein said housing has an outer diameter in the range of 1.5 mm to 8 mm.

8. The device of claim 7, wherein said housing has an outer diameter in the range of 2 mm to 3 mm.

9. The device of claim 8, wherein said housing has an outer diameter of 2.4 mm.

* * * * *